US012697503B2

(12) United States Patent　　　(10) Patent No.: US 12,697,503 B2

Gerstenmeier　　　(45) Date of Patent:　　　Aug. 4, 2026

(54) BODY IRRADIATING DEVICE

(71) Applicant: JK-HOLDING GMBH, Windhagen (DE)

(72) Inventor: Jürgen Gerstenmeier, Windhagen (DE)

(73) Assignee: JK-HOLDING GMBH, Windhagen (DE)

( * ) Notice: Subject to any disclaimer, the term of this patent is extended or adjusted under 35 U.S.C. 154(b) by 328 days.

(21) Appl. No.: 17/818,411

(22) Filed: Aug. 9, 2022

(65) Prior Publication Data

US 2022/0379136 A1　　　Dec. 1, 2022

Related U.S. Application Data

(63) Continuation of application No. PCT/DE2021/100143, filed on Feb. 12, 2021.

(30) Foreign Application Priority Data

Feb. 12, 2020　　(DE) ......................... 202020100756.4

(51) Int. Cl.
*A61N 5/06*　　　(2006.01)

(52) U.S. Cl.
CPC .... *A61N 5/0614* (2013.01); *A61N 2005/0636* (2013.01); *A61N 2005/0652* (2013.01);
(Continued)

(58) Field of Classification Search
CPC .......... A61N 5/0614; A61N 2005/0636; A61N 2005/0652; A61N 2005/0659; A61N 2005/0661; A61N 2005/0667
See application file for complete search history.

(56) References Cited

U.S. PATENT DOCUMENTS

| 5,445,608 A | 8/1995 | Chen et al. |
| 10,197,261 B1 | 2/2019 | Nakamura |

(Continued)

FOREIGN PATENT DOCUMENTS

| CN | 103562985 A | 2/2014 |
| CN | 107029357 A | 8/2017 |

(Continued)

OTHER PUBLICATIONS

Prindeze, et al., Mechanisms of action for light therapy: a review of molecular interactions, Experimental Biology and Medicine, vol. 237, pp. 1241-1248 2012.

(Continued)

*Primary Examiner* — Carl H Layno
*Assistant Examiner* — Aya Ziad Bakkar
(74) *Attorney, Agent, or Firm* — HESLIN ROTHENBERG FARLEY & MESITI P.C.

(57)　　　ABSTRACT

The invention relates to a body irradiating device, in particular for irradiating a body of a person or a part of a body of a person, in particular with cosmetically and hygienically useful radiation, comprising a radiation source with a base and at least one first LED chip which can emit a first radiation spectrum with a first radiation peak and at least one second LED chip which can emit a second radiation spectrum with a second radiation peak differing from the first radiation peak. A body irradiating device allowing the radiation spectrum of more than one LED chip to be combined and uniformly supplied to the human body is achieved in that the first LED chip and the second LED chip are arranged below a common lens in an LED package and can be controlled separately.

25 Claims, 5 Drawing Sheets

(52) U.S. Cl.
   CPC ................. *A61N 2005/0659* (2013.01); *A61N 2005/0661* (2013.01); *A61N 2005/0667* (2013.01)

(56) References Cited

U.S. PATENT DOCUMENTS

| | | | |
|---|---|---|---|
| 10,309,587 | B2 | 6/2019 | Aanegola et al. |
| 10,349,484 | B1 | 7/2019 | Zhang et al. |
| 11,717,698 | B1 | 8/2023 | Mcgrath, Jr. |
| 2003/0233138 | A1 | 12/2003 | Spooner |
| 2005/0065579 | A1 | 3/2005 | Chen et al. |
| 2010/0179622 | A1 | 7/2010 | Wagenaar Cacciola et al. |
| 2012/0043907 | A1 | 2/2012 | Lu et al. |
| 2013/0184693 | A1 | 7/2013 | Neev |
| 2014/0005756 | A1* | 1/2014 | Liu ...................... A61B 18/203 |
| | | | 607/90 |
| 2014/0207215 | A1 | 7/2014 | Fiset |
| 2014/0288351 | A1* | 9/2014 | Jones .................. A61N 5/0624 |
| | | | 607/90 |
| 2015/0097200 | A1 | 4/2015 | Bergmann et al. |
| 2016/0016001 | A1 | 1/2016 | Loupis et al. |
| 2016/0175550 | A1 | 6/2016 | Taylor |
| 2016/0276549 | A1 | 9/2016 | Yamashita et al. |
| 2017/0182332 | A1 | 6/2017 | Fiset |
| 2018/0021593 | A1 | 1/2018 | Vartanian et al. |
| 2018/0269360 | A1 | 9/2018 | Yeon et al. |
| 2018/0353770 | A1 | 12/2018 | Moffat |
| 2019/0074411 | A1 | 3/2019 | Schlosser et al. |
| 2020/0001105 | A1 | 1/2020 | Teegardin |
| 2021/0007824 | A1 | 1/2021 | Timoszyk et al. |
| 2021/0260400 | A1 | 8/2021 | Gerstenmeier |

FOREIGN PATENT DOCUMENTS

| | | |
|---|---|---|
| CN | 107708800 A | 2/2018 |
| DE | 102019119686 A1 | 1/2020 |
| EP | 2800605 B1 | 10/2017 |
| EP | 2301071 B1 | 8/2019 |
| EP | 3597268 A1 | 1/2020 |
| JP | 2017533074 A | 11/2017 |
| TW | 200939449 A | 9/2009 |
| TW | 201944430 A | 11/2019 |
| WO | 2006001928 A1 | 1/2006 |
| WO | WO2007114614 A1 | 10/2007 |

OTHER PUBLICATIONS

Slabke, LED Lighting Technology: Basic Knowledge for Planning, Selection, and Installation, H. Heenemann GmbH tt Co KG, ISBN 978-3-8007-4452-7 (E-Book), Berlin.
Light Emitting Diode, Wikipedia Article, Nov. 28, 2022.
Light Emitting Diode, Wikipedia Article, Dec. 10, 2022.

\* cited by examiner

BODY IRRADIATING DEVICE

CROSS REFERENCES TO RELATED APPLICATIONS

This application is based on, and claims priority to: PCT Patent Application No. PCT/DE2021/100143, filed on Feb. 12, 2021 and published as PCT Publication No. WO2021/160223A1; and German Patent Application No. DE202020100765.4, filed on Feb. 12, 2020. The contents of the prior patent applications are hereby incorporated by reference herein in their entirety.

TECHNICAL FIELD

The invention relates to a body irradiation device for the human body, comprising a radiation source with a base and at least one first LED chip, which can emit a radiation spectrum with a first radiation peak, and at least one second LED chip, which can emit a second radiation spectrum with a second radiation peak different from the first radiation peak.

BRIEF DESCRIPTION

Body irradiation devices for the human body are known from practice, which are designed in particular as an irradiation device in the form of a solarium with a lying surface or a stand-up tanner or an infrared treatment bed where the human body or parts of the human body are exposed to a radiation spectrum in certain wavelength ranges in order to influence the well-being, health, or regeneration of the human body. Known body irradiation devices partially use low-pressure radiation tubes and partially high-pressure radiation tubes, which emit a broad radiation spectrum and in which it may be necessary to arrange a filter in order to prevent harmful radiation from reaching the surface of the human body. A disadvantage of the body irradiation devices with low-pressure or high-pressure tubes is, in particular, that the radiation intensity varies greatly over the broad radiation spectrum, so that the correct dosing of the radiation and the application of the desired, particularly favorable, radiation peak are either not achieved or involve high radiation loss. In particular, combination treatments in which specific radiation peaks are to be applied to the body in combination are at most random and can barely be influenced in terms of their relative intensity.

In practice, body irradiation devices have been proposed, in which one LED chip is arranged below a lens in each case and emits a relatively narrow radiation spectrum with a comparatively defined radiation peak, wherein the difficulty here is to apply uniform radiation of different wavelengths to the human body so that a homogeneous application over the entire surface of the human body is achieved.

EP 2 800 605 B1 describes a body irradiation device for supporting the formation of vitamin D, in which different light sources, including a plurality of LED's, are specified which can emit a radiation spectrum, wherein the light source is arranged in a reflector designed as a concave mirror, and the radiation emitted by the light source is collimated by the reflector before it passes through a filter layer that allows a predetermined bandwidth of the radiation to pass through. A disadvantage here is that no uniform irradiation with defined coordination of several peaks within the radiation spectrum is possible. A further disadvantage is that a large installation space is required. Furthermore, the extinction of certain wavelengths by the filter layer causes a portion of the energy to remain unused.

U.S. 2005 006 55 79 A1 shows a body irradiation device which makes it possible to subject the body of a person or a part of the body of a person to radiation—in particular, infrared radiation—wherein the device is designed as a manually-operated device and has a circuit board. A lighting arrangement is connected to the circuit board via a conductor track, which lighting arrangement comprises one or more replaceable light-emitting elements—in particular, LED's. This light-emitting arrangement represents a radiation source that inherently has a base and comprises an LED, and thus also a chip for each replaceable light-emitting element, wherein the LED chip can emit a radiation spectrum with a radiation peak. Further light-emitting elements are arranged within the light-emitting arrangement, each of which also has one radiation peak, and the radiation spectrum of which differs from that of the first LED chip. The entire light-emitting arrangement is covered by a lens 102, which constitutes a transparent cover, but not an optical lens.

U.S. 2020 000 11 05 A1 shows a body irradiation device designed as a tanning device that is designed to irradiate the body of a person or parts of the body of a person with radiation of wavelengths that are specified in detail, in which radiation sources are provided which have a plurality of LED's, wherein the LED's can emit different radiation spectra, wherein the design of the visual appearance and the structural arrangement of the LED's are designed to be conventional.

U.S. 2012 004 39 07 A1 describes an irradiation device for irradiating plants, which irradiation device comprises a radiation source with a base of at least one first LED chip and a second LED chip, wherein the first LED chip emits a radiation spectrum that is different from the second LED chip and is greater than 400 nm—specifically, for example, red and blue—in the visible spectrum, so that their rather broadband radiation peaks are each different. The first LED chip and the second LED chip are arranged below a common lens in an LED package and can also be controlled separately. The irradiation device is not designed or suitable for irradiating a human body or a part of a human body, since a long-lasting irradiation with a correspondingly low intensity takes place over a comparatively long interval compared to the plants; shaded areas result if the irradiation device is moved closer to the irradiation target.

U.S. 2015 009 72 00 A1 describes an irradiation device for generating, in particular, visible light with a combination of LED's and a fluorescent material, the radiation spectrum of which turns out to be correspondingly wide and comparatively uniform. The irradiation device has a base on which a first LED chip, a second LED chip, a third LED chip, and a fourth LED chip are arranged, the radiation spectrum of which can be designed differently, wherein the LED chips are arranged below a common lens in an LED packageLED package, and the LED chips can be controlled separately. The first radiation peak generated by the first LED chip is between 430 nm and 455 nm or 479 nm, and the second radiation peak generated by the second LED chip is between 456 nm and 469 nm or 600 nm to 650 nm, wherein a first radiation peak generated by a third LED chip is between 600 nm and 650 nm in the first alternative. In this case, the fluorescent or excitable material radiates radiation with a radiation peak between 500 nm and 555 nm, wherein the radiation of the LED's and the radiation of the fluorescent material overlap. Use of only the LED's without fluorescent material is not provided for. The irradiation device is used, for example, as a table lamp or the like, but not for irradiating the human body. Furthermore, a method for producing an irradiation device is described.

It is the object of the invention to specify a body irradiation device by means of which the radiation spectrum of more than one LED chip can be combined and applied uniformly to the human body.

This object is achieved according to the invention by a body irradiation device having the features of an independent claim.

According to an aspect of the invention, a body irradiation device is provided, comprising a radiation source with a base and with at least one first LED chip which can emit a first radiation spectrum with a first radiation peak, and with at least one second LED chip which can emit a second radiation spectrum with a second radiation peak different from the first radiation peak, which device distinguishes further in that the first LED chip and the second LED chip are arranged below a common lens in an LED package and can be controlled separately. By arranging the first LED chip and the second LED chip below the common lens, radiation having the first radiation peak and radiation having the second radiation peak can be emitted uniformly through the common lens—preferably with a downstream collimation reflector for collimating the first radiation spectrum and the second radiation spectrum—so that the downstream area where a human body can lie is illuminated uniformly with the first radiation spectrum and the second radiation spectrum. A particularly homogeneous distribution of the radiation is thereby achieved; in particular, this also prevents intensity peaks from reaching the human body. Furthermore, as a result of being able to separately control the first LED chip and the second LED chip, the radiation intensity of the first radiation spectrum and of the second radiation spectrum can be individually adjusted and regulated, which enables not only the simultaneous irradiation with the first radiation spectrum and the second radiation spectrum, but, moreover, a coordination of the intensity peaks with each other with respect to the desired result. The separate regulation of the LED chips particularly preferably comprises the possibility of individually adjusting the intensity of the radiation of the different LED chips individually and independently of one another, whereby favorable peak ratios can be set which at the same time advantageously reduce the energy consumption. Moreover, it can be provided that the LED chips also be able to be contacted separately.

Here, the LED package is the housing in which the LED chips are accommodated. It is therefore actually an LED chip package. LED package is not to be understood to mean a housing in which one or more LED's are accommodated, which in turn themselves contain LED chips that are accommodated in an LED package. The LED package is equipped with contacts in order to contact the individual LED chips. The lens covering the LED package closes off the LED chip(s) accommodated in the LED package to the outside, so that the resulting LED can be used accordingly.

The body irradiation device is designed to irradiate the human body of a person or a part of the human body of a person, i.e., the body of a living creature or of an individual, including all limbs and surface regions—in particular, with cosmetically and hygienically useful radiation. As a result, it differs from irradiation devices that aim radiation at objects and for which no health restrictions with regard to, for example, dose and radiation spectrum have to be observed. Thus, in particular, individual or all limbs of a human being or possibly of another mammal can be regarded as bodies.

The radiation source preferably comprises at least one third LED chip which can emit a third radiation spectrum with a third radiation peak different from the first radiation peak and the second radiation peak, wherein the third LED chip is arranged with the at least one first LED chip and the at least one second LED chip below the common lens in an LED package and can be controlled separately from them. As a result, it is, advantageously, possible to also aim a third radiation spectrum with a third radiation peak homogeneously and uniformly, and independently of the intensity of the other two radiation peaks, at the human body, and thus to use three radiation spectra with three different radiation peaks uniformly, and in a manner where the intensities have been matched, to irradiate the human body. This makes it possible, in particular, to carry out complex combination treatments where, for example, the radiation spectra can be controlled simultaneously, in an overlapping manner and/or successively or in a pulsed manner, so that different aspects of body regeneration can be addressed simultaneously.

The radiation source preferably comprises at least one fourth LED chip which can emit a fourth radiation spectrum with a fourth radiation peak different from the first radiation peak and the second radiation peak and the third radiation peak, wherein the fourth LED chip is arranged with the at least one first LED chip and the at least one second LED chip and the at least one third LED chip below the common lens in an LED package and can be controlled separately from them. Separate regulation enables the individual control of all at least one first, second, third, and fourth LED chips, so that even complex treatment patterns with alternating or combined activated radiation peaks can be set.

The radiation source preferably comprises at least one fifth LED chip which can emit a fifth radiation spectrum with a fifth radiation peak different from the first radiation peak and the second radiation peak and the third radiation peak and the fourth radiation peak, wherein the fifth LED chip is arranged with the at least one first LED chip and the at least one second LED chip and the at least one third LED chip and the at least one fourth LED chip below the common lens in an LED package and can be controlled separately from them. Separate regulation enables the individual control of all at least one first, second, third, fourth, and fifth LED chips, so that even complex treatment patterns with alternating or combined activated radiation peaks can be set.

Thus, the body irradiation device can also be used in a versatile manner, since LED chips can also be located below the common lens which are not used in the same radiation treatment, but which allow for carrying out different treatments in one device (combination device). Thus, for example, a body irradiation device can have two LED chips used for a combined generation of previtamin D3, and/or two or more LED chips used for tanning, and/or two or more LED chips used for skin and wound regeneration, and/or two or more LED chips used for the (cosmetic) treatment of acne, below the same lens, which advantageously results in a multi-purpose device that is accordingly inexpensive to produce, purchase, and operate.

It is possible to also provide more than one first, second, etc., LED chip within the radiation source, e.g., two LED chips with a first radiation peak and an LED chip with a second radiation peak. In another embodiment, it can be provided, for example, that there be one more of the first LED chip than of the second LED chip. In yet another embodiment, it can be provided that there be one more of the second LED chip than of the third LED chip, so that a total of six LED's are provided in such an embodiment, viz., three of the first LED chip, two of the second LED chip, and one of the third LED chip. Expediently, no more than six LED chips are arranged below a common lens, wherein LED chips of similar type can also be jointly controlled and contacted.

While the radiation peaks of the first, second, etc., radiation peaks differ, this does not preclude that the associated radiation spectra may partially overlap. However, the resulting intensity and the radiation density of the overlap area are, expediently, smaller than each of the individual radiation peaks.

In addition to the radiation sources with LED chips, the body irradiation device can also have further radiation-generating means—for example, low-pressure tubes or high-pressure lamps.

It is possible to provide a universal base which can be equipped with different LED chips, wherein control takes place depending upon the LED chips provided.

The LED chips are, expediently, arranged on the base and covered by the lens forming a first primary lens. The lens can have a convex outer contour and concave inner contour in the manner of a focus lens, wherein the diameter of the lens is at least three times, and preferably at least four times, as large as the diagonal of the largest of the LED chips. Due to the distance at which the lens is in the projection from the LED chips, which is, expediently, at least as large as the diagonal of the corresponding chip, good distribution of the radiation of the LED chips is effected, even if they are not arranged centrically below the lens.

According to a favorable embodiment, it is provided for a filter layer to be arranged between the LED chips and the lens. The filter layer can be designed as a filter glass with a short-pass and/or long-pass filter and serves in particular to filter out radiation with critical radiation wavelengths below and/or above a wavelength defined as threshold value. In the case of broad radiation spectra of high-pressure and/or low-pressure lamps, such filter layers are expedient; in the case of LED chips with correspondingly narrow radiation spectra, they may be dispensed with under certain circumstances. A filter is particularly expedient in the case of relatively small wavelengths and/or for peaks that are close to one another.

According to another advantageous embodiment, it is provided for the lens to have an integrated filter arrangement, which prevents undesired radiation spectra from passing through and thus eliminates them. The filter arrangement is, expediently, a filter with a short-pass and/or long-pass filter, which prevents radiation that is outside a desired spectrum from passing through and thus eliminates it.

However, an embodiment is preferred in which the radiation spectra of the LED chips are limited, such that no filter is required. This advantageously also brings about a favorable temperature development of the radiation source, because the filtered waves otherwise cause an increase in the temperature, and thus an increased cooling effort and poorer efficiency.

A particularly favorable irradiation result ensues when the radiation peaks of the LED chips are defined by a wavelength, and if the spectrum of the LED chips is more than two thirds, preferably more than three quarters, and particularly preferably more than nine tenths, within a bandwidth, which can be calculated by the product of the wavelength (in nm) and a factor F (i.e., wavelength×F), wherein factor F is selected such that it is between 1+/−0.005 and 1+/−0.05, and thus surrounds the radiation peak from both sides. As a result, the radiation spectrum is concentrated substantially within a width of approximately equal size on both sides of the peak, such that a particularly effective treatment of the human body with defined radiation peak is achieved. At the same time, the extremely narrow deviation around the radiation peak ensures that harmful radiation is emitted in, at most, a minor quantity. Particularly preferably, even a proportion of 99%, preferably 99.9%, and particularly preferably 99.99%, is within the specified limit.

Preferably, radiation peak of the LED chips, i.e., for example, of the first, of the second, of the third, of the fourth, and of the fifth LED chip, is selected from the group comprising 290 nm+/−2 nm, 297 nm+/−2 nm, 310 nm+/−5 nm, 365 nm+/−10 nm, 620 nm+/−15 nm, 660 nm+/−15 nm, 465 nm+/−20 nm, 740 nm+/−20 nm, and 840 nm+/−20 nm; and. In this case, certain wavelengths can be combined to form therapeutically and/or cosmetically favorable combinations with matched radiation intensities, thereby achieving physiological effects in the body to be irradiated. The selection of certain radiation peaks reduces the irradiation and thus possible damage or stress on the human body from radiation that is not, or not optimally, effective, and the body is thus prevented from being damaged. The tolerances indicated in each case reflect the fact that the radiation peak of the respective LED chip cannot be reproduced exactly and always identically, but may vary within narrow limits.

The aforementioned radiation peaks belong to the group of cosmetically and hygienically useful radiation, irrespective of any medical effect that may exist at the same time. In particular, the cosmetically and hygienically useful radiation has a photobiological effect on an irradiated individual. The cosmetically and hygienically useful radiation impinges on the skin of the individual, but can also penetrate into deeper regions of the body, depending upon the specific wavelength. The effect comprises, for example, tanning of the skin, but also further physiological and psychological effects resulting from the irradiation. Cosmetically and hygienically useful radiation comprises the spectrum of ultraviolet (UV) radiation outside the UV-C spectrum, visible (VIS) radiation, and near infrared (nIR) radiation. In this case, the UV radiation outside the UV-C spectrum has wavelengths in the spectrum between 280 nm and approximately 380 nm, the VIS radiation has wavelengths in the spectrum between approximately 380 nm and approximately 780 nm, and the nIR radiation has wavelengths in the spectrum between approximately 780 nm and 1,400 nm. The specified spectra merge into one another. Depending upon the cosmetic or hygienic application, irradiation can be concentrated on a partial spectrum of the stated spectra. For this purpose, arrangements that emit cosmetically and hygienically useful radiation can also be dedicated to individual wavelengths—for example, to UV radiation. It can be seen that the above-specified preferred radiation peaks of the LED chips all fall in the range of cosmetically and hygienically useful radiation. However, the list of the specifically mentioned radiation peaks of the LED chips and/or their arbitrary combinations of two or more radiation peaks, which are hereby expressly mentioned as being part of the disclosure, is not exhaustive.

An interesting aspect is, further, that the combination treatment allows not only for exposing the human or animal body to radiation of the corresponding wavelengths, but also for correlating these radiation peaks in a targeted manner. Thus, the intensity of the radiation can be adjusted in relation to one another, as can the duration and/or the order of irradiation.

It is preferably provided for at least one radiation peak emitted by one of the LED chips, e.g., that of the first LED chip or of a further LED chip, to have a wavelength that lies outside the spectrum of visible light. In contrast to body irradiation devices which emit exclusively a broad spectrum of visible light, a body irradiation device is here provided that also has at least one radiation peak with a wavelength in the range of ultraviolet (UV) radiation outside the UV-C spectrum and/or near infrared (nIR) radiation. It is possible for further radiation peaks to have a wavelength in the range of the spectrum of visible (VIS) radiation and/or outside thereof. In this way, irradiation modes that provide radiation in the invisible range can also conveniently be set.

Preferably, the at least one radiation peak, which is outside the spectrum of visible light, has a wavelength of less than 380 nm and is thus within the range of the spectrum of ultraviolet (UV) radiation outside the UV-C spectrum. It is possible to provide several radiation peaks from this spectrum. The at least one radiation peak, which is outside the spectrum of visible light, has, for example, a wavelength selected from the group comprising 290 nm+/−2 nm; 297 nm+/−2 nm; 310 nm+/−5 nm; and 365 nm+/−10 nm.

The at least one radiation peak, which is outside the spectrum of visible light, alternatively has a wavelength of greater than 780 nm and is thus in the range of the spectrum of near infrared (nIR) radiation. It is possible to provide several radiation peaks from this spectrum. The at least one radiation peak, which is outside the spectrum of visible light, has, for example, a wavelength selected from the group comprising 840 nm+/−20 nm.

The aforementioned radiation peaks, which are outside the spectrum of visible light, can also be combined with further radiation peaks that are emitted by other LED chips and which are included in the spectrum of visible light.

Preferably, a collimation reflector for collimating the radiation is arranged downstream of the lens forming a primary lens and collimates the radiation of all LED chips uniformly, and thus forms a secondary lens. For this purpose, the collimation reflector is preferably designed in the manner of a truncated cone or a rotational paraboloid, which is cut off at the end, with a strongly reflecting inner circumference made, for example, of aluminum, as a result of which the radiation exiting through the lens is homogenized and, in particular, no relative intensity peaks arise in the region of the irradiated surface. It is particularly surprising here that the same collimation reflector can be used even for wavelength ranges which differ by up to a factor of two, and, nevertheless, the emitted radiation impinges almost homogeneously on the human body. To regulate the impingement intensities, the LED chips can be controlled accordingly, which can be easily achieved by calibrating the body irradiation device.

The collimating reflector, expediently, has a small opening on the side facing the lens and a larger opening on the side facing away from the lens, which opening is, expediently, circular. The radiation passing through the lens enters through the small opening, and collimated radiation exits through the large opening. The collimating reflector is thus arranged completely upstream of the LED package and the lens.

According to a favorable aspect, it is provided for more than half of the LED chips to be arranged eccentrically to a center point defined by the projection of the apex of the lens on the base. Surprisingly, it has been found that at least two LED chips with a uniform emission can be arranged on the base in a particularly favorable manner if neither the first LED chip nor the second LED chip is arranged exactly on the center point, but is arranged at a distance from the center point in each case. This initially leads to less homogeneous illumination, which is, however, almost completely compensated for especially by downstream collimation reflectors, whereas an arrangement of one of the LED chips on the center point is homogenized more poorly by the downstream collimation reflector.

Preferably, in case of more than two LED chips, one of the LED chips is arranged on a center point defined by the projection of the apex of the lens on the base, wherein the chip is preferably selected in this case that has a low radiation intensity and, accordingly, a high energy consumption, if the intensity is to be increased.

However, it is, expediently, provided that all LED chips be arranged eccentrically to a center point defined by the projection of the apex of the lens on the base, as a result of which a uniform illumination, which is in particular established by the downstream collimation reflector, can be achieved for all LED chips and their respective radiation spectra.

According to a preferred embodiment, it is provided that at least one of the LED chips be able to emit radiation in a pulsed manner. Depending upon the wavelengths—preferably at wavelengths of more than 280 nm, and preferably of more than 700 nm—the pulsed radiation can achieve favorable effects, particularly in the treatment of the human body, and in this case can be particularly stimulating. It is possible to provide the pulsing of the one LED chip simultaneously or alternately with the pulsing of the other LED chip. The pulsed LED chips are, expediently, used in the range of visible light and of the near infrared spectrum. However, it is also possible to pulse the LED chips in the range of the UV-A and UV-B spectra.

During pulsing of the LED chips, the "pulse width ratio" parameter, i.e., the ON/OFF ratio or the ratio of the duration of radiation emission to the duration of radiation non-emission, can be set within wide limits in a first advantageous embodiment. In a first preferred embodiment, the ON duration is equal to the OFF duration. In a second preferred embodiment, the ON duration is between 25% and 200% longer than the OFF duration. Surprisingly, by pulsing the LED chips in the aforementioned pulse width ratios, a significantly better effect of irradiation appears to be achieved than with continuous irradiation.

During pulsing of the LED chips, the frequency parameter, i.e., the number of ON/OFF pulses per unit of time, can be set within wide limits in a second advantageous embodiment, which can optionally be implemented at the same time as the first embodiment. A particularly effective frequency is selected between 0.25 Hz and 500 Hz, preferably between 1 Hz and 100 Hz, particularly preferably between 8 Hz and 15 Hz, and preferably at 10 Hz. A further favorable frequency lies in the frequency band that is greater than or equal to the frequency that is perceived by the human eye to be intermittent, i.e., for example, above 50 Hz. Here, for example, a frequency of 60 Hz, 120 Hz, or 240 Hz is considered.

The separate pulsing of the first LED chips, second LED chips, etc., independently of one another, albeit possibly coordinated with one another, is also realized by the separate regulation of the LED chips, without these further features having to be provided in every embodiment.

Expediently, a plurality of lenses are arranged on the carrier, each of which covers several LED chips in one LED package in each case. According to a preferred development, all radiation sources formed in such a way on the carrier are of the same design, so that each lens covers the same number with the same LED chips. However, it is possible to design the radiation sources provided on an irradiation system in various ways.

According to a favorable development, it is provided for the body irradiation device to further comprise a carrier on which a plurality of radiation sources are arranged, each having several LED chips below a common lens. It is expediently provided here for the same LED chips to be uniformly controlled on the carrier.

A favorable embodiment advantageously provides for twenty radiation sources or an integer multiple thereof to be arranged on the carrier. As a result, a carrier can be equipped in each case with twenty radiation sources having several LED chips which can be arranged and operated in a modular manner within a body irradiation device, and can nevertheless be easily exchanged.

It is, advantageously, provided that the base of the radiation sources be in each case arranged on the carrier. The base can, for example, be provided in one piece as a recess on the carrier, or it can be glued, clamped, or arranged on the carrier—for example, in a recess provided for this purpose. The base is preferably the foundation of the LED package, which moreover has an annular wall, thus forming a type of chamber or receptacle. An underside facing away from the base is preferably flat and can be fixed on a planar side of the carrier 41.

According to another advantageous embodiment, it is provided for all radiation sources on the carrier to be designed identically, so that the respective LED chips can be controlled jointly, in parallel, or in series. Thus, the first LED chips are activated jointly, the second LED chips are activated jointly, etc. Alternatively, the radiation sources on the carrier can be designed differently; in this case, the LED chips must be individually controlled. Combinations of both embodiments are also possible, i.e., for example, an array of identically-designed first radiation sources and, additionally, individual second radiation sources designed differently therefrom.

The body irradiation device expediently has an irradiation space in which the human body to be irradiated is encompassed in the manner of a tunnel, wherein the tunnel can be designed either as a vertically-aligned tunnel with a movable wall element or as a bed with a pivotable cover element. It is possible to apply an air flow to the irradiation tunnel for dissipating heat, which air flow cools the interior of the tunnel.

In this case, the body irradiation device preferably comprises a housing which at least partially surrounds a tunnel-like irradiation space for a person to be irradiated and has at least one accommodation space for the light sources. A partition wall of the housing between the accommodation space and the irradiation space is, advantageously, made of a material that is transparent to the radiation of the radiation sources. The radiation of the radiation sources is here directed from the accommodation space into the irradiation space.

One advantageous embodiment provides for the first radiation peak to be 290 nm+/−2 nm and for the second radiation peak to be 297 nm+/−2 nm. With this combination within the UV-B spectrum, the provitamin D3 can conveniently be produced, wherein, at the same time, damage to the DNA of the treated individual is particularly low.

Another advantageous embodiment provides for the first radiation peak to be 310 nm+/−5 nm and for the second radiation peak to be 365 nm+/−10 nm. With this combination of a wavelength from the UV-B spectrum and a wavelength from the UV-A spectrum, tanning of the human skin can be favorably achieved by pigment discoloration.

Another advantageous embodiment provides for the first radiation peak to be 620 nm+/−15 nm and for the second radiation peak to be 660 nm+/−15 nm. With this combination of a wavelength from the visible (VIS) spectrum, cosmetic effects, skin rejuvenation, and/or wound healing can be achieved and/or promoted.

In an advantageous development, it is then provided for the third radiation peak to be 740 nm+/−20 and for the fourth radiation peak to be 840 nm+/−20 nm. In addition, a wellness effect and a regeneration of tendons, fascia, and muscles is thereby promoted and/or achieved.

In a further development, it is then provided for the fifth radiation peak to be 465 nm+/−20 nm. This also reduces acne of the irradiated skin.

Yet another advantageous embodiment provides for the first radiation peak to be 465 nm+/−20 nm and for the second radiation peak to be 660 nm+/−20 nm and for the third radiation peak to be 840 nm+/−20 nm. This, advantageously, helps, in particular, acne of the skin to recede.

According to an aspect of the invention, the use of the body irradiation device as described above is provided for cosmetic, medical, psychological, wellness, and regeneration treatments. In particular, the body irradiation device can be provided for the non-therapeutic treatment of the human and/or animal body—for example, for psychological treatment or for cosmetic treatment.

According to an aspect of the invention, a method for the preferably non-therapeutic irradiation of a person with cosmetically and hygienically useful radiation is provided, comprising a radiation source with a base and with at least one first LED chip, which can emit a radiation spectrum with a first radiation peak, and with at least one second LED chip, which can emit a second radiation spectrum with a second radiation peak different from the first radiation peak, wherein the method distinguishes in that the first LED chip and the second LED chip are arranged below a common lens and are controlled separately. As a result, it is, advantageously, possible to match the intensity of the radiation spectra of the first LED chip and of the second LED chip and, at the same time, to ensure that the radiation emitted by the radiation source impinges homogeneously on the individual to be irradiated. The above-described body irradiation device, including all of its optional further developments, can be provided for the method. Preferably, in accordance with the above description, third, fourth, and fifth LED chips are also possible, which are arranged below the common lens and are controlled separately. The method advantageously provides for the irradiation of a human body of a person or of a part of a human body of a person. As a result, it differs from irradiation methods that aim radiation at objects and for which no health restrictions with regard to dose and radiation spectrum have to be observed. By accommodating several LED chips in one LED package, it is possible to arrange the body irradiation device close to the body to be irradiated and, nevertheless, to achieve a homogeneous application with all radiation peaks in a narrow space. Due to the arrangement of the body irradiation device close to the body, the radiation acts more intensively, and the duration of treatment is, advantageously, reduced.

Further advantages, developments, and properties of the invention emerge from the following description of preferred exemplary embodiments and from the dependent claims.

DRAWINGS

The invention is explained in more detail below with reference to the accompanying drawings using preferred exemplary embodiments.

DETAILED DESCRIPTION

Figure 1:
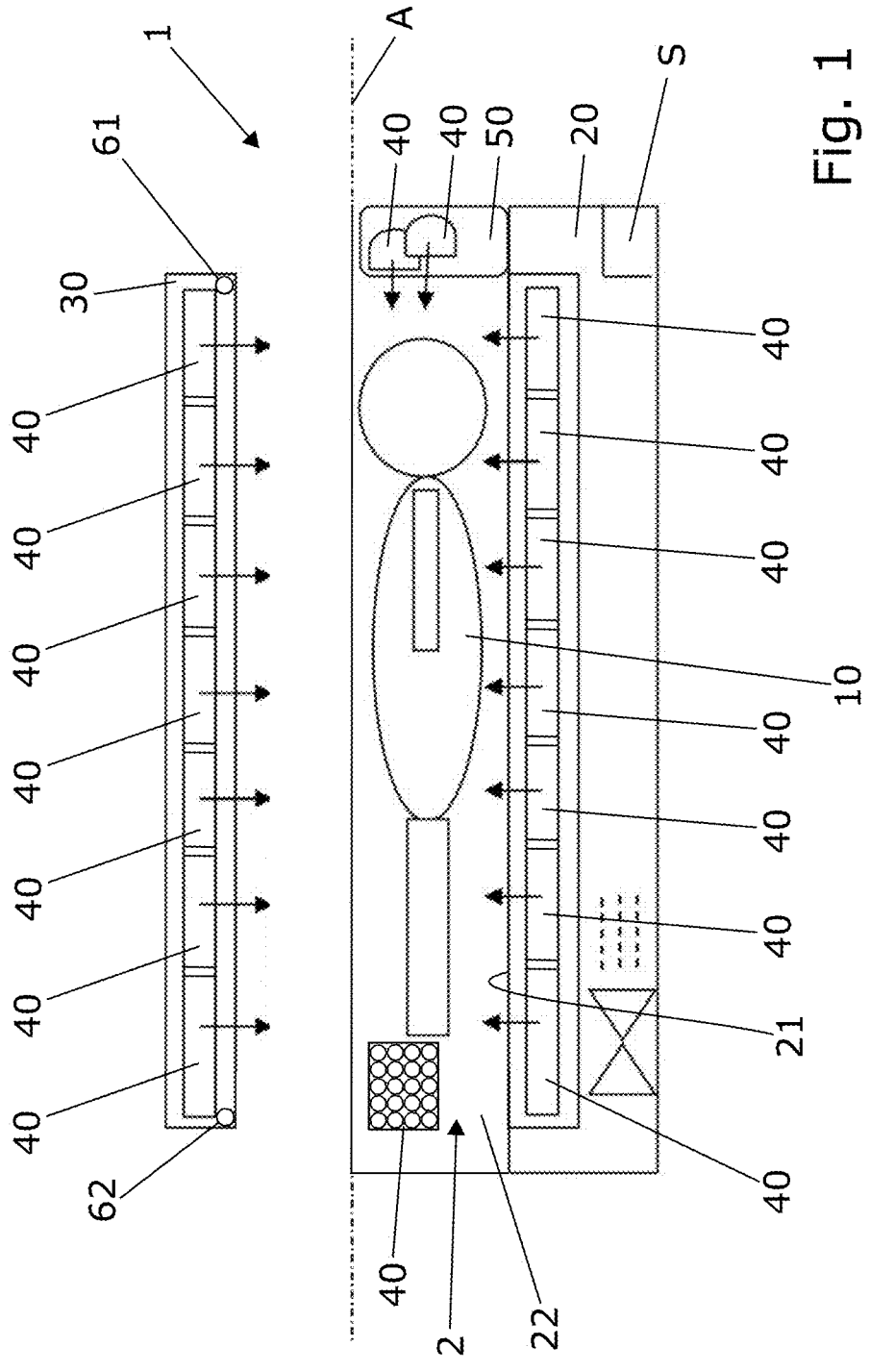
FIG. 1 shows a schematic side view of a preferred exemplary embodiment of a body irradiation device according to the invention.

FIG. 1 shows a body irradiation device 1 for irradiating a person, schematically illustrated with their human body 10, with cosmetically and hygienically useful radiation, the device comprising a lower housing part 20 and an upper housing part 30 which are connected to one another in an articulated manner along an axis A. The upper housing part 30 can be pivoted upwards in order to clear the access for the user 10 and can be pivoted downwards so that the housing parts 20, 30 enclose a tunnel-like tube 2 in which the user 10 lies.

The housing parts 20, 30 are encapsulated in acrylic glass, wherein a lying surface 21 made of acrylic glass is formed in the lower housing part 20. It is possible to equip the lying surface with a silicone mat, which is connected to the lying surface 10 and which is flexible, and offers a pleasant surface feel for the person 10. The acrylic glass and the silicone mat are each permeable for at least parts of the cosmetically and hygienically useful radiation.

Irradiation modules 40, which are directed towards the tube 2 in the housing parts 20, 30, are arranged in the lower housing part 20 and in the upper housing part 30 in each case. The irradiation modules 40 are rectangular and are arranged next to each other and, in the lower housing part 20, parallel to the lying surface 21. Furthermore, irradiation modules 40, which can irradiate the individual 10, are also provided on the vertical section 22 of the lower housing part 20 that is approximately perpendicular to the lying surface 21. In the upper housing part 30, a plurality of irradiation modules 40 are arranged in a row, in each case abutting one another, wherein the irradiation modules arranged in a row are angled with respect to the adjacent row by an angle in order to be able to follow the semicircular contour of the upper housing part 30 within the housing part 30. Depending upon the radius and size of the irradiation modules, the angle is between 5° and 25°, and preferably approximately 10°.

A shoulder tanning device 50 is arranged at one front end of the tube 2, which shoulder tanning device irradiates in particular the head and the shoulder of the user 10, wherein two further irradiation modules 40 are arranged within the shoulder tanning device 50.

The irradiation modules 40 are connected to a controller S of the device 1.

The body irradiation device 1 also has a series of further components which improve the irradiation experience. A touch-sensitive flatscreen is provided, as a first interface for communicating with the individual 10, on an inner side of the upper housing part 30, which flatscreen allows inputs by the individual 10 and also enables the playback of an entertainment program. Furthermore, speakers are arranged in the head region of the individual 10 which allow for an acoustic experience such as, e.g., background music to enhance the irradiation experience—possibly in interaction with the visual entertainment program. A second interface for communicating with the individual 10 is provided on an outer side of the upper housing part 30, via which programs can be selected. A voice control is provided as a third interface for communicating with the individual 10, which voice control detects voice inputs via a speaker attached to at least one of the housing parts, evaluates the voice inputs in a computer-assisted manner, and converts them into control commands for the body irradiation device 1. Furthermore, the body irradiation device 1 comprises ventilation of the tube 2 that supplies fresh air and discharges heated air in the tube. Furthermore, the body irradiation device 1 has a fragrancing device which makes it possible to perfume the fresh air with one of a plurality of scents. Finally, the body irradiation device 1 also comprises all electrical and electronic components necessary for operation.

Figure 2:
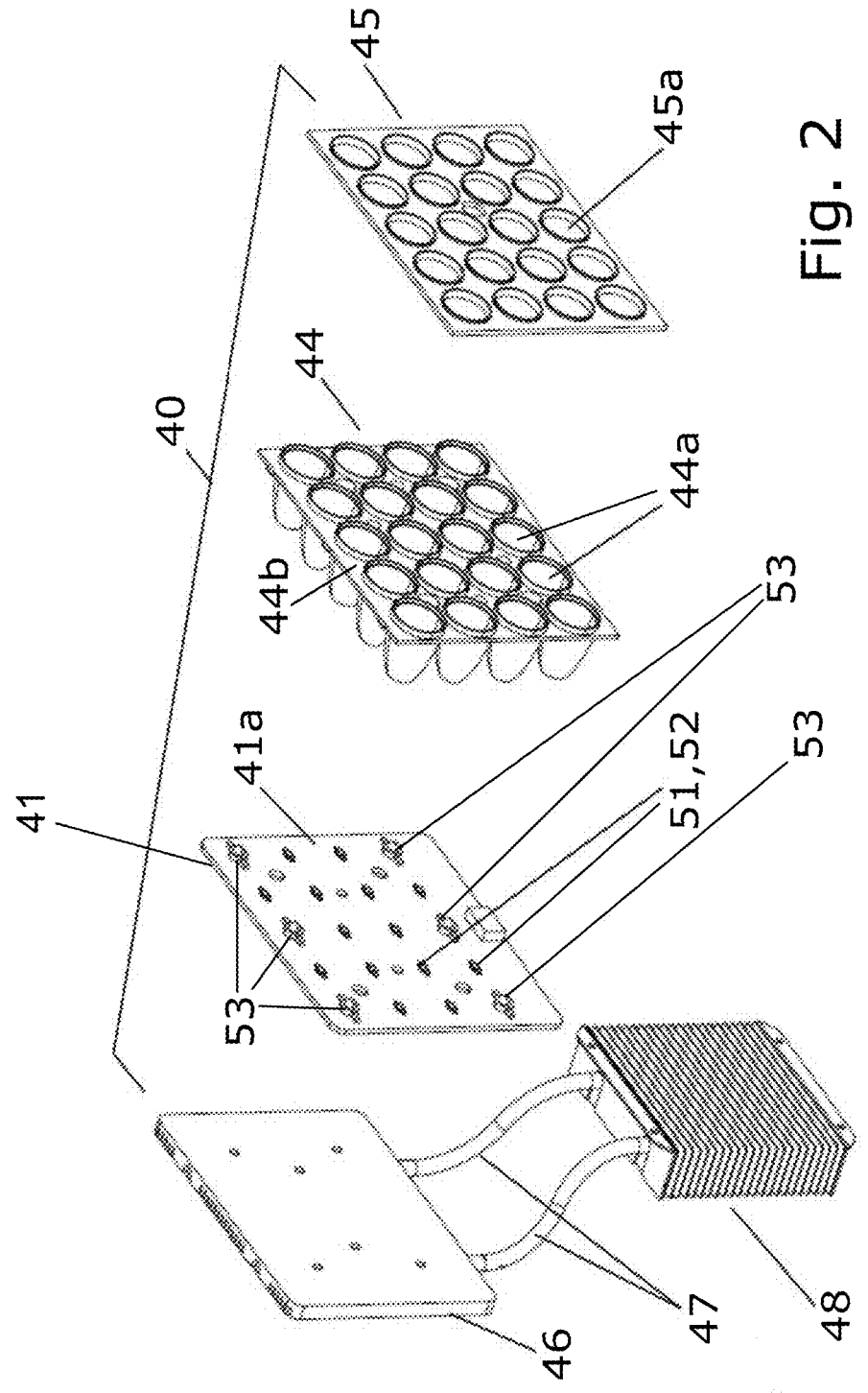
FIG. 2 shows an exploded view of an irradiation module installed in the body irradiation device of FIG. 1.

FIG. 2 shows an exploded view of an irradiation module 40. It can be seen that a plurality of twenty radiation sources 50 in total, each comprising at least one first LED chip 51 and one second LED chip 52 that are contacted with an electrical energy supply via the carrier 41, are attached to a respective area 41a of a carrier 41. It is also possible to provide the LED chips in a different number and/or arrangement than as present in the 4×5 array arrangement.

It can be seen in FIG. 2 that one common lens 53 is shown on the carrier 41, for a total of six LED's 51, 52, which lens is fixed to the surface 41a and has an outwardly-curved shape and is permeable to the radiation of the LED chips 51, 52.

A structural unit 44 with 20, identically-formed collimation reflectors 44a is provided upstream of the carrier 41 with the LED's 42, 43, wherein the hole size of the collimation reflectors 44a is matched to the lenses 53. For this purpose, the reflectors 44a are connected in a region, which is spaced apart from the LED's 42, 43, with a disk 44b which has openings for the collimation reflectors 44a, so that the structural unit 44 can be handled like a part.

An annular disk 45 is arranged upstream of the structural unit 44, which annular disk has a number of circular recesses 45a, corresponding to the number of collimation reflectors 44a, in a plate body which are coated with a fluorescent material in their inner circumference. When the LED's 51, 52 are caused to emit the radiation, this radiation excites the fluorescent material of the rings 45a, and, due to the illumination of the rings 45a taking place in the visible range, it can be seen that the LED's 51, 52 also emit radiation.

A heat transfer plate 46 is arranged on the side of the carrier 41 facing away from the LED's 51, 52, which heat transfer plate is designed as a plate body and is intended to dissipate the heat produced during operation of the LED's 42, 43. For this purpose, the heat transfer plate 46 is connected via a first cooling line 47 and a second cooling line 47 to a heat sink 48 designed as a heat exchanger, wherein a circulating cooling fluid is provided between the heat transfer plate 46 formed with cavities, the first cooling line 47, the heat sink 48, and the second cooling line 47. Cooling of the heat transfer plate 46 can be effected in particular by phase transformation of the cooling fluid between the heat transfer plate 46, on the one hand, and the heat sink 48, on the other.

The irradiation modules 40 installed in the housing part 20 or housing part 30 are all constructed identically; it is understood, however, that the irradiation modules can also be constructed and/or controlled differently, depending upon the light sensitivity of certain body regions of the user 10.

A first sensor 61 is provided in the upper housing part 30, which determines the properties of the body of the user 10—in particular, their height, width, circumference, and the position of the arms, legs. The radiation modules 40 are adjusted in their radiation intensity according to the detected properties of the body. Thus, for example, the irradiation module 40 which is facing away from the head end can be completely switched off when the legs of the user no longer cover this irradiation module 40.

The sensor 61 can, alternatively or additionally, detect certain skin characteristics of the body of the user 10, e.g., the presence of tattoos, of burns, of wounds, of moles, of scars, of white spots, of pigment disorders, the current tan, and the skin type. This second sensor, which also can be designed as a camera and to which an evaluation logic unit is connected, detects coloring and contrasts of the skin with a high resolution and evaluates the acquired images in order to determine the mentioned characteristics of the body. Depending upon the skin features, the irradiation module 40 is then operated at reduced power if, based upon the skin characteristics detected, there is a risk that the skin could burn during normal irradiation and exposure.

Finally, a second sensor 62 is arranged in the upper housing part 30 and detects the radiation of the irradiation modules 40 or of the associated LED's 51, 52. The second sensor 62 or its evaluation unit compares the detected radiation with, for example, target values stored in the controller S, and, in response to a deviation of the detected values from the target values, the controller causes the operating parameters of the irradiation modules 40 to be adjusted so as to be set to the target value.

Figures 3A, 3B:
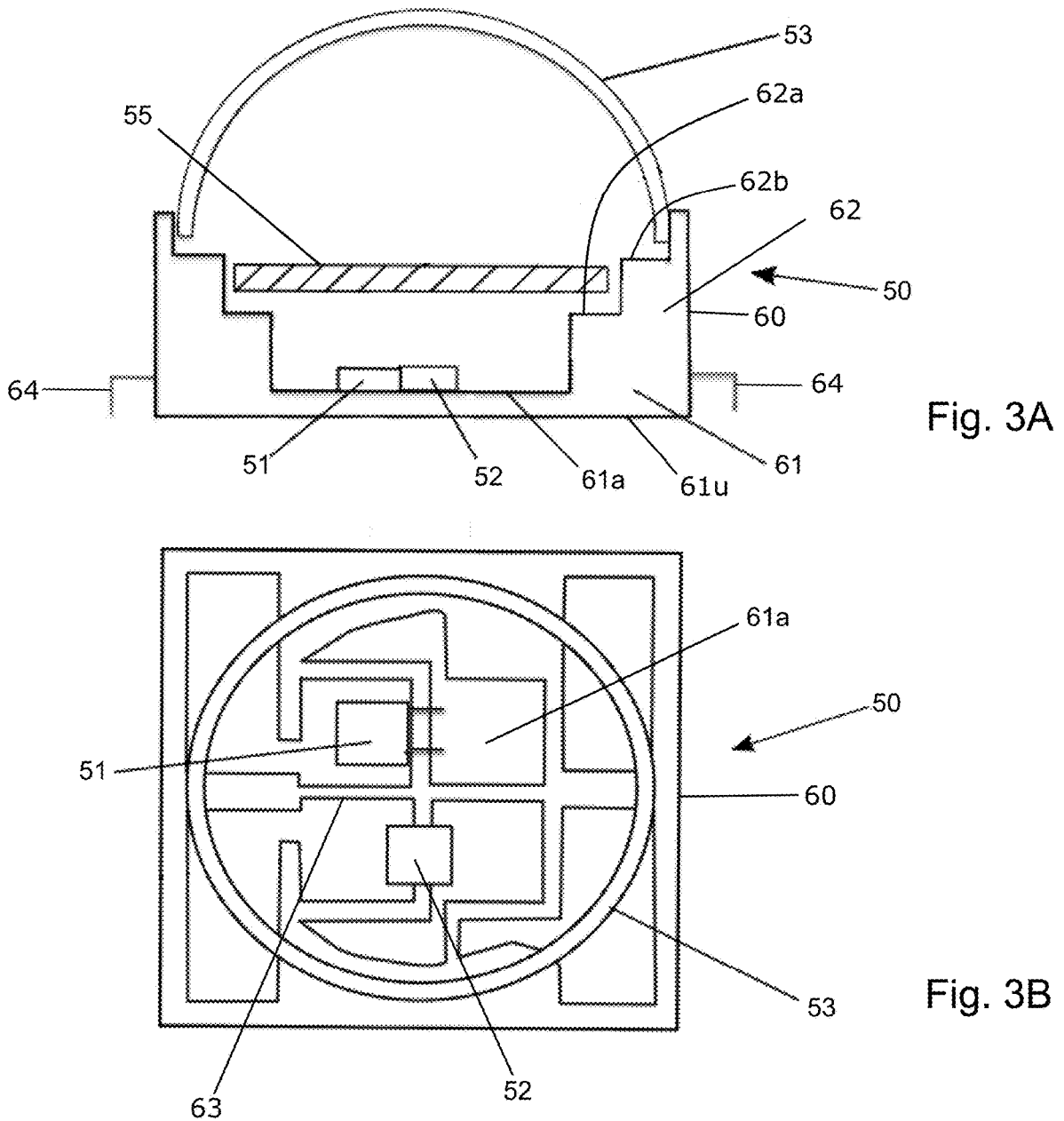
FIG. 3A shows a cross-section through a radiation source from the irradiation module from FIG. 2.
FIG. 3B shows a plan view of the radiation source from FIG. 3A.

FIGS. 3A and 3B show a cross-section and a plan view of a first embodiment of the radiation source 50 which explain the structure of the radiation source 50 schematically, but are not true-to-scale. The radiation source 50 is accommodated in an LED package 60 made of an electrical insulator such as plastic or ceramic, which has a rectangular—in the present case, square-layout and which has a base 61, the underside 61$u$ of which can in turn be connected, e.g., glued, to a surface of the carrier 41—for example, a highly heat-conductive plate made of aluminum. Alternatively, the LED package 60 can also be mounted on a socket that is attached to the carrier 41. Furthermore, electrical lines are laid on the carrier 41. Typically, the carrier 41 has approximately twenty LED packages 60 arranged in a 5×4 array.

On a base 61$a$, facing away from the underside, which is substantially circular and surrounded by a ring region 62, the first LED chip 51 and the second LED chip 52 are each arranged eccentrically to a center point of the base 61$a$. The two LED chips 51, 52 are contacted on the base 61$a$ via corresponding conductor tracks 63. An electrical connection of the radiation source 50 is denoted by 64. The base 61$a$ forms a depression above which a filter layer 55 is arranged on an annular shoulder 62$a$ of the annular region 62. The LED package 60 forms a depression, having an opening only in one direction, several of which may be arranged on the carrier 41.

The filter layer 55 filters the radiation emitted by the LED chips 51, 52 within predetermined wavelength limits, which may be prespecified for health reasons, for example. The lens 53 is supported and held circumferentially in a clamped manner on an annular flange region 62$b$ that is located further outwards and further away from the base 61$a$. In addition, the lens can also be glued onto the annular flange region. It can be seen that further base regions are provided on the base 61$a$ in which further LED chips can be placed. It can be seen that only radiation filtered through the filter layer 55 can exit the lens 53.

Figures 4A, 4B:
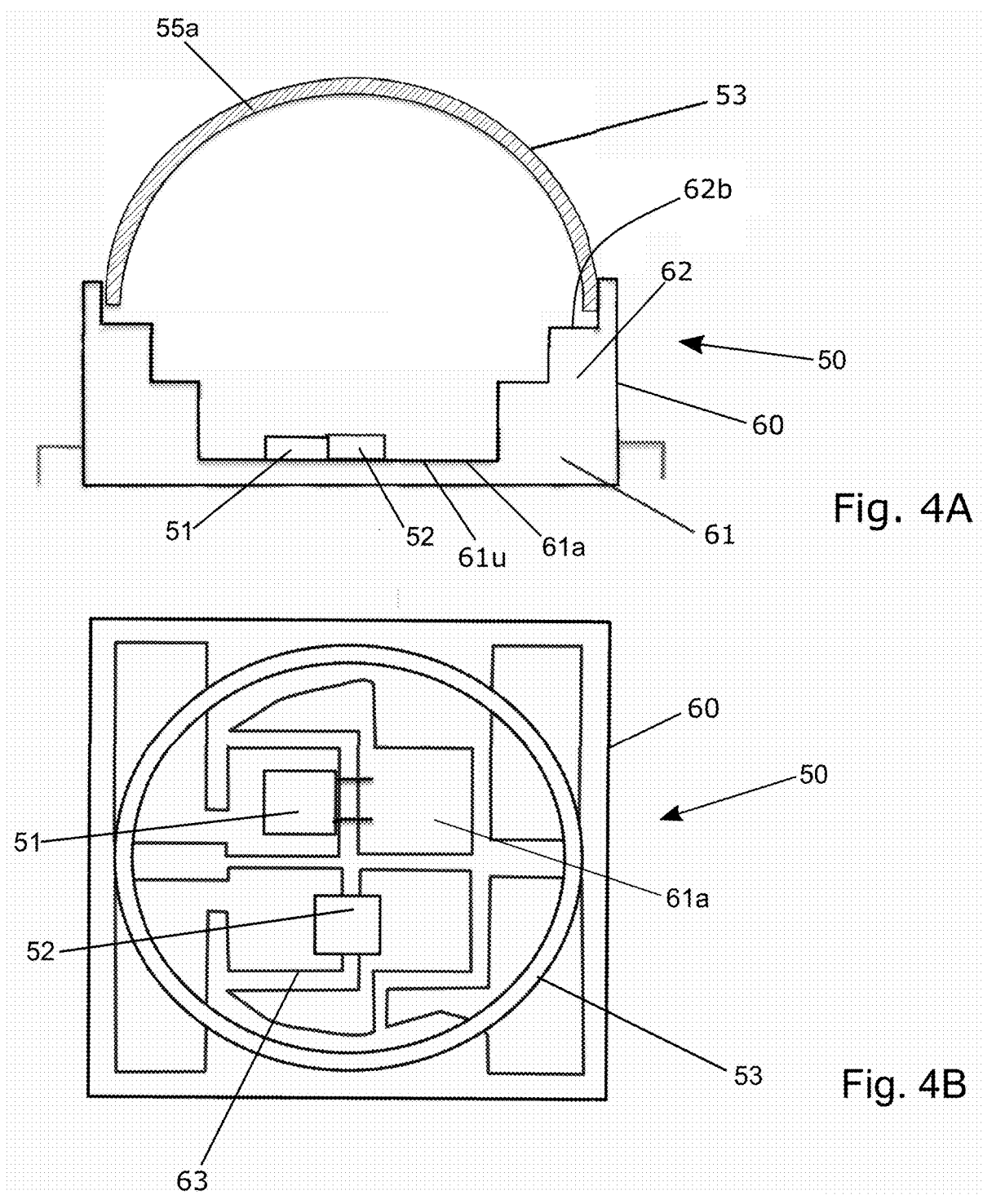
FIG. 4A shows a cross-section through another radiation source from the irradiation module from FIG. 2.
FIG. 4B shows a plan view of the radiation source from FIG. 4A.

FIGS. 4A and 4B show a cross-section and a plan view of another embodiment of the radiation source 50. In contrast to the embodiment according to FIGS. 3A and 3B, no filter layer 55 is provided here. However, a filter arrangement 55$a$, which filters the radiation emitted by the LED chips 51, 52 within predetermined wavelength limits, is integrated into the lens 53. It is possible to provide the filter layer 55 and the filter arrangement 55$a$ in a combined manner in a radiation source 50. In another embodiment, no filtering of the radiation is performed.

Example 1

The radiation source 50 of the body irradiation device 1 comprises a first LED chip 51 with a first radiation peak of 290 nm and a second LED chip 52 with a second radiation peak of 297 nm. The intensity ratio (level) of the first radiation peak to the second radiation peak is 1:5. The treatment serves to produce provitamin D3, wherein DNA damage to the irradiated body of the individual 10 is minimal.

Figure 5:
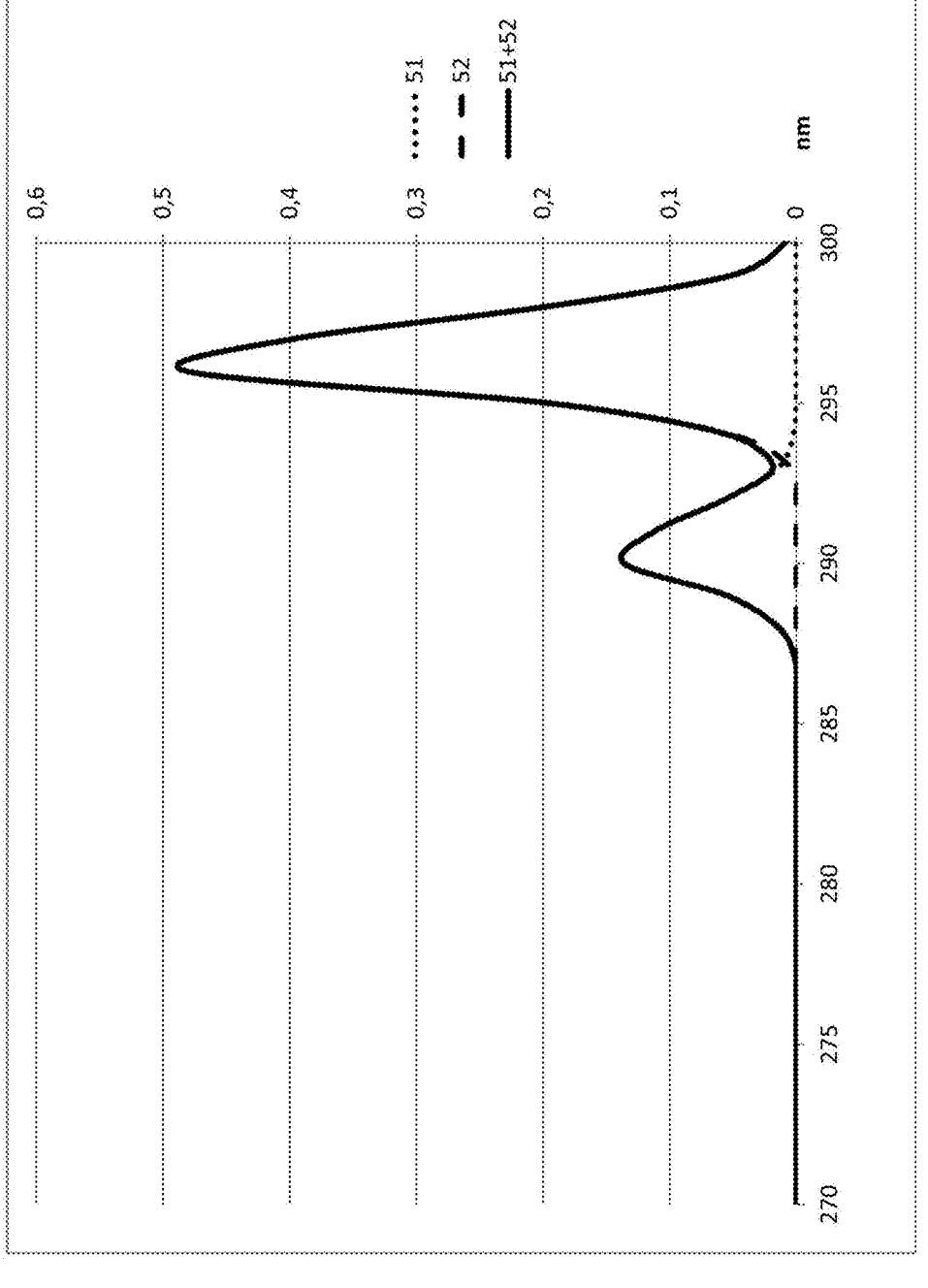
FIG. 5 shows the intensity of the radiation of two LED chips in a radiation source according to example 1.

FIG. 5 shows the intensity profile of the first radiation spectrum of the first LED chip 51 and of the second radiation spectrum of the second LED chip 52 with the aforementioned radiation peaks in a diagram above the wavelength. The resulting curve is also shown.

Example 2

The radiation source 50 of the body irradiation device 1 comprises a first LED chip 51 with a first radiation peak of 310 nm and a second LED chip 52 with a second radiation peak of 365 nm. The intensity ratio (level) of the first radiation peak to the second radiation peak is 3:1, but can be varied as desired. The treatment serves to excite the pigmentation of the skin of the individual 10—generally also referred to as tanning.

Example 3

The radiation source 50 of the body irradiation device 1 comprises a first LED chip 51 with a first radiation peak of 620 nm and a second LED chip 52 with a second radiation peak of 660 nm. The intensity ratio (level) of the first radiation peak to the second radiation peak is 2:1, wherein adjustment is possible within wide limits. The treatment serves for skin rejuvenation, wound healing, and cosmetic purposes.

Example 4

The radiation source 50 of the body irradiation device 1 comprises a first LED chip 51 with a first radiation peak of 465 nm and a second LED chip 52 with a second radiation peak of 660 nm and a third LED chip (not shown) with a third radiation peak of 840 nm. The intensity ratio (level) of the first radiation peak to the second radiation peak to the third radiation peak is 1:2:1, wherein adjustment is possible within wide limits. The treatment serves for acne prevention and acne reduction in the skin of the person 10.

Example 5

The radiation source 50 of the body irradiation device 1 comprises a first LED chip 51 with a first radiation peak of 620 nm and a second LED chip 52 with a second radiation peak of 660 nm and a third LED chip (not shown) with a third radiation peak of 740 nm and a fourth LED chip (not shown) with a fourth radiation peak of 840 nm. The intensity ratio (level) of the first radiation peak to the second radiation peak to the third radiation peak to the fourth radiation peak is 2:1:1:2, wherein adjustment is possible within wide limits. The treatment serves for skin rejuvenation, wound healing, and cosmetic purposes, and in particular for the regeneration of tendons, fascia, and muscles of the person 10.

Example 6

The radiation source 50 of the body irradiation device 1 comprises a first LED chip 51 with a first radiation peak of 465 nm and a second LED chip 52 with a second radiation peak of 620 nm and a third LED chip (not shown) with a third radiation peak of 660 nm and a fourth LED chip (not shown) with a fourth radiation peak of 740 nm and a fifth LED chip (not shown) with a fifth radiation peak of 840 nm. The intensity ratio (level) of the first radiation peak to the second radiation peak to the third radiation peak to the fourth radiation peak to the fifth radiation peak is 1:1:1:1:1, wherein adjustment is possible within wide limits. The treatment serves for skin rejuvenation, wound healing, and cosmetic purposes, and in particular for the regeneration of tendons, fascia, and muscles, and for acne prevention and reduction in the skin of the person 10.

In all the examples listed above, irradiation by one of the LED chips can take place both continuously and intermittently—for example, in a pulsed manner. In the case of pulsed irradiation, the irradiation duration is, advantageously, twice as long as the pause between two successive irradiations.

The above examples show that the targeted treatment of the body with radiation of certain wavelengths can achieve very advantageous effects. However, there is a risk of overdosing if the individual wants to force a therapeutic success. Therefore, it is provided in an advantageous embodiment that at least one and preferably both of the two LED chips from Example 2 be additionally installed in the radiation source 50, so that the onset of tanning prevents misuse.

It can be seen from the above examples that, in the case of a radiation source 50 with, for example, 5 dedicated LED chips, a plurality of irradiation combinations can be provided in which not all LED chips are necessarily used, depending upon the desired result. Thus, the radiation source 50 from Example 6 can also produce the irradiation patterns of Examples 3, 4, and 5.

The LED chips have been numbered above in each case according to increasing wavelength. It is understood that the assignment to the first, second, etc., of several LED chips can be done in any way desired. For example, in Examples 4, 5, or 6, the radiation peak of 840 nm, which is outside the visible spectrum, can be assigned to the first or second LED chip. In the examples with two LED chips, the assignment to the radiation peaks can be interchanged, for example, since the order is random.

The invention has been explained above with reference to exemplary embodiments in which the irradiation peaks have been selected from a group having certain wavelengths. It has to be understood that further LED chips with irradiation peaks at other wavelengths can readily be added to the group.

The invention has been explained above with reference to an exemplary embodiment in which a filter layer 55 is provided between the LED chips 51, 52 and the lens 53, or in which the lens 53 has an integrated filter arrangement 56. It has to be understood that, in the case of a narrow spectrum of the radiation produced by the LED chips, a filter layer and/or a filter arrangement can be dispensed with; the same applies to LED chips the radiation spectrum of which is in the visible or near-infrared range.

The invention has been explained above with reference to exemplary embodiments in which only one LED chip with a specific radiation peak is provided in the radiation source. It has to be understood that, irrespective of the further LED chips with other radiation peaks, more than one LED chip with the specific radiation peak may also be provided.

The invention has been explained above with reference to an exemplary embodiment in which the carrier 41 of the irradiation module 40 is substantially rectangular and has an array of 4×5 radiation sources 50. It has to be understood that the carrier 41 can also have a different shape, e.g., a square or hexagonal or linear shape, and that the radiation sources 50 can also be arranged differently on the carrier 41.

The invention has been explained above with reference to an exemplary embodiment in which the carrier 41 is connected to a heat transfer plate 46 which is connected to a heat exchanger via cooling lines 47. It has to be understood that the heat exchanger 48 can, at the same time, be connected to a further carrier 41 via further cooling lines, and that it is also possible to connect several heat transfer plates via connecting lines to the heat exchanger 48 to form a closed system.

The invention has been explained above with reference to an exemplary embodiment in which all irradiation modules 40 in the device 1 are designed in the same way. It has to be understood that the irradiation modules 40 for the shoulder and head region, the irradiation modules in the lower housing part 20, and the irradiation modules in the upper housing part 30 can also be designed differently, and in particular can also have a different number of LED's.

The invention has been explained above with reference to an exemplary embodiment in which the irradiation modules 40 are arranged in a stationary manner in the housing parts 20, 30 and are controlled substantially in response to data acquired by the first sensor 61 and the second sensor 62. It has to be understood that, instead of being controlled electrically, the irradiation modules 40 can also be adjustable with regard to their distance to the body of the user 10—for example, via pneumatic, hydraulic, mechanical, or electrical adjustment devices.

The invention has been explained above with reference to an exemplary embodiment in which the device 1 has a stationary lower part 20 and an upper housing part 30 that can be pivoted down onto the lower part 20, wherein the user 10 rests on a lying surface 21 of the lower housing part 20. It has to be understood that the device can also be designed in the form of a stand-up tanner in which the two housing parts are arranged substantially vertically, and in which the user is essentially standing on the floor during irradiation and is surrounded by the housing parts. It has further to be understood that the device can also be designed in the form of a vertical irradiation device or irradiation module which is arranged on a preferably mobile stand and can be positioned, for example, above a bed on which a user lies. Such irradiation devices can be used, for example, for tanning the face or another body part, or else for other cosmetic and hygienic applications.

The invention has been explained above with reference to an exemplary embodiment in which a sensor 61, 62 detects properties of the device 1 or of the individual 10. It has to be understood that several sensors can also be provided for this purpose, and that the data obtained by the sensors can also be stored in order to document the proper adjustment of the device.

The invention has been explained above with reference to an exemplary embodiment in which the radiation sources 50 have been combined with their base 61*a* to form irradiation modules 40. It has to be understood that no irradiation modules with several individual radiation sources 50 need be on a common carrier, but that each radiation source 50 can also be arranged on a separate carrier, making it possible to follow more easily, in particular, the curved shape of the upper housing part 30. Accordingly, the radiation source 50 is then connected directly to the body irradiation device 1.

What is claimed is:

1. A body irradiation device for irradiating at least a part of a body of a person with cosmetically and hygienically useful radiation, comprising: a plurality of irradiation modules positioned throughout the body irradiation device, each irradiation module of the plurality of irradiation modules individually controlled by a controller, wherein each irradiation module comprises: a plurality of radiation sources, wherein each radiation source of the plurality of radiation sources comprises an LED package, the LED package comprising an LED package base, at least one first LED chip which can emit a first radiation spectrum with a first radiation peak, at least one second LED chip which can emit a second radiation spectrum with a second radiation peak different from the first radiation peak, and a lens covering said LED package base, said at least one first LED chip and said at least one second LED chip; and a housing comprising a lower housing part and an upper housing part connected to one another in an articulated manner along an axis, wherein the housing is configured to at least partially surround a tunnel-like irradiation space for a person to be irradiated and that has a plurality of accommodation spaces positioned in the lower housing part and the upper housing part for the irradiation modules to be disposed in, wherein partition walls of the housing between the plurality of accommodation spaces and the irradiation space are made of a material that is transparent to the radiation of the radiation sources of the irradiation modules, wherein the radiation of the radiation sources is directed from the accommodation spaces into the irradiation space; and wherein the at least one first LED chip and the at least one second LED chip of each radiation source can be controlled separately by the controller, wherein a radiation of said at least one first LED chip and a radiation of said at least one second LED chip of each radiation source are uniformly emitted through said respective lens of each radiation source such that the irradiation space is illuminated uniformly with the first radiation spectrum and the second radiation spectrum.

2. The body irradiation device according to claim 1, wherein at least one radiation peak of the radiation peak of the at least one first LED chip and the radiation peak of the at least one second LED chip has a wavelength that is outside a spectrum of visible light.

3. The body irradiation device according to claim 2, wherein said at least one radiation peak of the radiation peak of the at least one first LED chip and the radiation peak of the at least one second LED chip has a wavelength of less than 380 nm, and wherein said at least one radiation peak has a wavelength selected from a group comprising 290 nm+/−2 nm; 297 nm+/−2 nm; 310 nm+/−5 nm; 365 nm+/−10 nm.

4. The body irradiation device according to claim 2, wherein said at least one radiation peak having a wavelength that is outside a spectrum of visible light has a wavelength greater than 780 nm, and wherein said at least one radiation peak having a wavelength that is outside a spectrum of visible light has a wavelength selected from a group comprising 840 nm+/−20 nm.

5. The body irradiation device according to claim 1, wherein the LED comprises at least one third LED chip which can emit a third radiation spectrum with a third radiation peak different from the first radiation peak and the second radiation peak, and which is arranged with the at least one first LED chip and the at least one second LED chip below said lens in the LED package and can be controlled separately from said at least one first LED chip and said at least one second LED chip.

6. The body irradiation device according to claim 5, wherein the LED comprises at least one fourth LED chip which can emit a fourth radiation spectrum with a fourth radiation peak different from the first radiation peak, the second radiation peak, and the third radiation peak, and which is arranged with the at least one first LED chip, the at least one second LED chip, and the at least one third LED chip below said lens in the LED package and can be controlled separately from said at least one first LED chip, said at least one second LED chip and said at least one third LED chip.

7. The body irradiation device according to claim 6, wherein the LED comprises at least one fifth LED chip which can emit a fifth radiation spectrum with a fifth radiation peak different from the first radiation peak, the second radiation peak, the third radiation peak, and the fourth radiation peak, and which is arranged with the at least one first LED chip, the at least one second LED chip, the at least one third LED chip, and the at least one fourth LED chip below said lens in the LED package and can be controlled separately from said at least one first LED chip, said at least one second LED chip, said at least one third LED chip, and said at least one fourth LED chip.

8. The body irradiation device according to claim 1, wherein the LED chips are arranged on the LED package base and surrounded by a ring region having an annular flange, and wherein the lens covering the LED chips is a first primary lens supported on said annular flange.

9. The body irradiation device according to claim 1, wherein a filter layer is arranged between the LED chips and the lens.

10. The body irradiation device according to claim 1, wherein the lens has an integrated filter arrangement.

11. The body irradiation device according to claim 1, wherein at least the at least one first LED chip is selected from a group comprising a radiation peak with a wavelength 290 nm+/−2 nm; 297 nm+/−2 nm; 310 nm+/−5 nm; 365 nm+/−10 nm; 620 nm+/−15 nm; 660 nm+/−15 nm; 465 nm+/−20 nm; 840 nm+/−20 nm; and 740 nm+/−20 nm.

12. The body irradiation device according to claim 1, wherein a collimation reflector for collimating the radiation is arranged downstream of the lens and collimates the radiation of all LED chips arranged under said lens uniformly.

13. The body irradiation device according to claim 1, wherein more than half of the LED chips are arranged eccentrically to a center point defined by a projection of an apex of the lens onto the LED package base.

14. The body irradiation device according to claim 1, wherein at least one of the LED chips can be controlled to emit radiation in a pulsed manner.

15. The body irradiation device according to claim 1, further comprising a carrier on which a plurality of radiation sources are arranged.

16. The body irradiation device according to claim 15, wherein the LED package base of the radiation sources is in each case arranged on the carrier.

17. A human body irradiation device for irradiating a body of a human person with cosmetically and hygienically useful radiation, comprising: a plurality of irradiation modules positioned throughout the body irradiation device, each irradiation module of the plurality of irradiation modules individually controlled by a controller, wherein each irradiation module comprises: a plurality of radiation sources, wherein each radiation source of the plurality of radiation sources comprises an LED package with an LED package base, at least one first LED chip which can emit a first radiation spectrum with a first radiation peak, at least one second LED chip which can emit a second radiation spectrum with a second radiation peak different from the first radiation peak, and an LED package lens, wherein the LED package lens covers the LED package base, the at least one first LED chip and the at least one second LED chip to enclose the LED package, a housing comprising a lower housing part and an upper housing part connected to one another in an articulated manner along an axis, wherein the housing is configured to at least partially surround a tunnel-like irradiation space configured for accommodating said body to be irradiated, wherein the housing comprises a plurality of accommodation spaces positioned in the lower housing part and the upper housing part for the radiation sources irradiation modules to be disposed in, a controller, and a sensor arranged in said irradiation space, wherein the at least one first LED chip of each radiation source and the at least one second LED chip of each radiation source can be controlled separately by said controller, wherein partition walls of the housing between the plurality of accommodation spaces and the irradiation space are made of a material that is transparent to the radiation of said at least one radiation sources of the irradiation modules, wherein the radiation of said at least one radiation source is directed from the accommodation space into the irradiation space, wherein the at least one first LED chip of each radiation source and the at least one second LED chip of each radiation source are selected from a group comprising a radiation peak with a wavelength 290 nm+/−2 nm; 297 nm +/−2 nm; 310 nm+/−5 nm; 365 nm+/−10 nm; 620 nm+/−15 nm; 660 nm+/−15 nm; 465 nm +/−20 nm; 840 nm+/−20 nm; and 740 nm+/−20 nm, wherein said sensor is configured to detect the radiation in the tunnel-like irradiation space, wherein the radiation detected by said sensor is provided to the controller, and wherein said at least one first LED chip of each radiation source and said at least one second LED chip of each radiation source are controlled by said controller to uniformly emit combined radiation through said respective LED package lens of each radiation source such that the irradiation space is illuminated uniformly with the combined first radiation spectrum and the second radiation spectrum.

18. The human body irradiation device according to claim 17, wherein at least one LED chip of the at least one first LED chip and the at least one second LED chip is capable to be controlled to emit radiation in a pulsed manner.

19. The human body irradiation device according to claim 18, wherein at least one of a frequency parameter and a pulse width parameter can be set for said at least one LED chip capable to be controlled to emit radiation in a pulsed manner.

20. The human body irradiation device according to claim 18, wherein the first radiation spectrum of the at least one first LED chip and the second radiation spectrum of the at least one second LED chip are narrow, and wherein the radiation of the at least one first LED chip and the radiation of the at least one second LED chip reaches the irradiation space without passing a filter.

21. A human body irradiation device for irradiation treatment of one of a body of a person and a part of a body of a person with cosmetically and hygienically useful radiation, comprising: a housing comprising a lower housing part and an upper housing part connected to one another in an articulated manner along an axis, a plurality of accommodation spaces positioned in the lower housing part and the upper housing part for the irradiation modules to be disposed in, a plurality of carriers arranged in said plurality of accommodation spaces, each carrier being provided with a plurality of irradiation modules positioned throughout the body irradiation device, each irradiation module of the plurality of irradiation modules individually controlled by a controller, wherein each irradiation module comprises: a plurality of LEDs, the LEDs comprising an LED package, and a controller, wherein each LED package comprises an LED package base arranged on the carrier, at least one first LED chip arranged on said base which can emit a first radiation spectrum with a first radiation peak, and at least one second LED chip arranged on said base which can emit a second radiation spectrum with a second radiation peak different from the first radiation peak, and an LED package lens configured as primary lens, wherein the primary lens is covering the LED package base, the at least one first LED chip of each radiation source and the at least one second LED chip of each radiation source, wherein the at least one first LED chip of each radiation source and the at least one second LED chip of each radiation source can be controlled separately by said controller, wherein a collimation reflector for collimating the radiation is arranged downstream each respective primary lens of each radiation source and uniformly collimates the radiation of said at least one first LED chip of each radiation source and said at least one second LED chip of each radiation source, wherein a partition wall delimiting said plurality of accommodation spaces of the housing made of a material that is transparent to the radiation of said at least one first LED chip of each radiation source and said at least one second LED chip of each radiation source are arranged downstream the collimation reflector, such that a homogeneous distribution of the radiation of said at least one first LED chip of each radiation source and said at least one second LED chip of each radiation source arranged in said LED package are obtained such that said one of said body of a person and said part of the body of the person can be homogeneously treated close to said partition wall of the housing.

22. The body irradiation device according to claim 21, wherein the housing at least partially surrounds a tunnel-like irradiation space for a person to be irradiated, wherein a partition wall of the housing between the accommodation space and the irradiation space is made of a material that is transparent to the radiation of the radiation sources, wherein the radiation of the radiation sources is directed from the accommodation space into the irradiation space.

23. The body irradiation device according to claim 21, comprising a stand on which said housing is arranged in at least one of a height-adjustable manner and a pivotable manner.

24. The human body irradiation device according to claim 21, wherein the LED package comprises, arranged on said LED package base and below said primary lens, at least one third LED chip which can emit a third radiation spectrum with a third radiation peak different from the first radiation peak and the second radiation peak, wherein said least one third LED chip can be controlled separately from said at least one first LED chip and said at least one second LED chip by said controller.

25. The human body irradiation device according to claim 21, further comprising an adjustment device for adjusting a distance of at least one carrier to the body of the person responsive to a sensor detecting the radiation of the LEDs.

* * * * *